US00PP29181P2

(12) United States Plant Patent
Barends

(10) Patent No.: US PP29,181 P2
(45) Date of Patent: Apr. 3, 2018

(54) ***PELARGONIUM* PLANT NAMED 'DUEPELSURNEVIOL17'**

(50) Latin Name: *Pelargonium×hortorum*
Varietal Denomination: Duepelsurneviol17

(71) Applicant: DUMMEN GROUP B.V., De Lier (NL)

(72) Inventor: Eveline Barends, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,740

(22) Filed: Feb. 22, 2017

(51) Int. Cl.
*A01H 5/02* (2006.01)

(52) U.S. Cl.
USPC ..... Plt./329
CPC ..... *A01H 5/0277* (2013.01)

(58) Field of Classification Search
USPC ..... Plt./329, 330
CPC ..... A01H 5/0277
See application file for complete search history.

*Primary Examiner* — Kent L Bell
(74) *Attorney, Agent, or Firm* — C. A. Whealy

(57) ABSTRACT

A new and distinct cultivar of *Pelargonium* plant named 'Duepelsurneviol17', characterized by its upright and rounded plant habit; vigorous growth habit; freely basal branching habit; dark green-colored leaves with a distinct zonation pattern; early and freely flowering habit; semi-double red purple-colored flowers; and good garden performance and high temperature tolerance.

1 Drawing Sheet

Botanical designation: *Pelargonium×hortorum.*
Cultivar denomination: 'DUEPELSURNEVIOL17'.

BACKGROUND OF THE INVENTION

The present invention relates to a new and distinct cultivar of *Pelargonium* plant, botanically known as *Pelargonium×hortorum*, commonly referred to as Zonal Geranium, and hereinafter referred to by the name 'Duepelsurneviol17'.

The new *Pelargonium* plant is a product of a planned breeding program conducted by the Inventor in Kako, Ethiopia and De Lier, The Netherlands. The objective of the breeding program is to create new freely-branching and freely-flowering *Pelargonium* plants with attractive leaf and flower coloration.

The new *Pelargonium* plant originated from a cross-pollination made by the Inventor in October, 2012 in Koka, Ethiopia of a proprietary selection of *Pelargonium×hortorum* identified as code designation PL-1129, not patented, as the female, or seed, parent with a proprietary selection of *Pelargonium×hortorum* identified as code designation PL-1500, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands in June, 2013.

Asexual reproduction of the new *Pelargonium* plant by vegetative terminal cuttings in a controlled greenhouse environment in De Lier, The Netherlands since July, 2013 has shown that the unique features of this new *Pelargonium* plant are stable and reproduced true to type in successive generations.

SUMMARY OF THE INVENTION

Plants of the new *Pelargonium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duepelsurneviol17'. These characteristics in combination distinguish 'Duepelsurneviol17' as a new and distinct *Pelargonium* plant:

1. Upright and rounded plant habit.
2. Vigorous growth habit.
3. Freely basal branching habit.
4. Dark green-colored leaves with a distinct zonation pattern.
5. Early and freely flowering habit.
6. Semi-double red purple-colored flowers.
7. Good garden performance and high temperature tolerance.

Plants of the new *Pelargonium* differ primarily from plants of the female parent selection in growth habit as plants of the female parent selection are less vigorous and smaller than plants of the new *Pelargonium.*

Plants of the new *Pelargonium* differ primarily from plants of the male parent selection in flower petal color as plants of the male parent selection have dark red-colored flower petals.

Plants of the new *Pelargonium* can be compared to plants of *Pelargonium×hortorum* 'Duevineon', disclosed in U.S. Plant Pat. No. 18,480. In side-by-side comparisons, plants of the new *Pelargonium* differ primarily from plants of 'Duevineon' in plant habit as plants of the new *Pelargonium* are more freely branching and denser than plants of 'Duevineon'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant.

The photograph is a side perspective view of a typical flowering plant of 'Duepelsurneviol17' grown in a container.

DETAILED BOTANICAL DESCRIPTION

The aforementioned photograph and following observations, measurements and values describe plants grown during the summer in 25-cm containers in a glass-covered greenhouse in Rheinberg, Germany and under cultural practices typical of commercial Zonal Geranium production. During the production of the plants, day temperatures ranged from 17° C. to 30° C., night temperatures ranged from 10° C. to 20° C. and light levels averaged 135 watt/$m^2$. Plants were eight weeks old when the photograph was taken and 25 weeks old when the description was taken. In the detailed description, color references are made to The Royal Horticultural Society Colour Chart, 2007 Edition, except where general terms of ordinary dictionary significance are used.

Botanical classification: *Pelargonium×hortorum* 'Duepelsurneviol17'.

Parentage:

*Female, or seed, parent*.—Proprietary selection of *Pelargonium×hortorum* identified as code designation PL-1129, not patented.

*Male or pollen parent*.—Proprietary selection of *Pelargonium×hortorum* identified as code designation PL-1500, not patented.

Propagation:

*Type*.—By vegetative terminal cuttings.

*Time to initiate roots, summer*.—About 18 days at temperatures ranging from 22° C. to 30° C.

*Time to initiate roots, winter*.—About 21 days at temperatures ranging from 22° C. to 30° C.

*Time to produce a rooted young plant, summer*.—About 25 days at temperatures ranging from 22° C. to 30° C.

*Time to produce a rooted young plant, winter*.—About 28 days at temperatures ranging from 20° C. to 25° C.

*Root description*.—Medium in thickness, fibrous; typically grey white in color, actual color of the roots is dependent on substrate composition, water quality, fertilizer type and formulation, substrate temperature and physiological age of roots.

*Rooting habit*.—Moderately freely branching, medium density.

Plant description:

*Plant habit*.—Upright and rounded plant habit; densely foliated.

*Growth and branching habit*.—Vigorous growth habit; moderate growth rate; freely basal branching habit with about eleven basal branches developing per plant.

*Plant height, to top of floral plane*.—About 34.5 cm.

*Plant height, to top of foliar plane*.—About 25.7 cm.

*Plant width*.—About 53.5 cm.

*Lateral branches*.—Length: About 23.5 cm. Diameter: About 8 mm. Internode length: About 3 cm. Strength: Moderately strong. Aspect: Mostly upright. Texture: Pubescent. Color: Close to 143B.

Leaf description:

*Arrangement*.—Alternate; simple.

*Length*.—About 7.4 cm.

*Width*.—About 10.6 cm.

*Shape*.—Reniform.

*Apex*.—Rounded.

*Base*.—Cordate.

*Margin*.—Crenate.

*Venation pattern*.—Palmate.

*Texture, upper surface*.—Pubescent.

*Texture, lower surface*.—Smooth, glabrous.

*Color*.—Developing leaves, upper surface: Close to 146B. Developing leaves, lower surface: Close to 146C. Fully expanded leaves, upper surface: Close to 137A; venation, close to 137A. Fully expanded leaves, lower surface: Close to 137B; venation, close to 143C. Zonation pattern: Distinct. Distance from leaf margin: About 1.4 cm. Width: About 1.9 cm. Color: Close to 147A.

*Petioles*.—Length: About 7 cm. Diameter: About 2 mm. Texture, upper and lower surfaces: Smooth, glabrous. Color, upper and lower surfaces: Close to 143B.

Flower description:

*Flower arrangement*.—Semi-double round flowers arranged in rounded hemispherical umbels arising from apical leaf axils; umbels displayed above the foliar plane on strong peduncles; flowers face upright to outwardly.

*Fragrance*.—None detected.

*Quantity of flowers*.—Freely flowering habit; about 36 flowers and flower buds per umbel and numerous umbels developing per plant during the flowering season.

*Flowering season*.—In The Netherlands, flowering is continuous from spring through the summer; early flowering habit, plants begin flowering about eight weeks after planting.

*Flower longevity*.—Individual flowers last about five to seven days on the plant; flowers persistent.

*Umbel height*.—About 7.5 cm.

*Umbel diameter*.—About 12.7 cm.

*Flower diameter*.—About 3.6 cm by 4.5 cm.

*Flower depth (height)*.—About 2.2 cm.

*Flower buds*.—Length: About 1.6 cm. Diameter: About 6 mm. Shape: Ovoid. Color: Close to 143B.

*Petals and petaloids*.—Quantity per flower: About eight. Length: About 2.7 cm. Width: About 2.6 cm. Shape: Obovate. Apex: Round. Base: Attenuate. Margin: Sinuate. Texture, upper and lower surfaces: Smooth, glabrous. Color: When opening and fully opened, upper surface: Close to N66A; venation, close to N66A; color becoming closer to 42A with development. When opening and fully opened, lower surface: Close to N57B; venation, close to N57B; color becoming closer to N66A with development.

*Sepals*.—Quantity per flower: Five arranged in a single whorl. Length: About 1.2 cm. Width: About 3 mm. Shape: Ensiform. Apex: Acuminate to apiculate. Base: Acute. Margin: Entire. Texture, upper and lower surfaces: Smooth, glabrous. Color, upper and lower surfaces: Close to 143C.

*Peduncle* (*umbel stem*).—Length: About 12.5 cm. Diameter: About 4 mm. Strength: Moderately strong. Aspect: Mostly upright. Texture: Smooth, glabrous. Color: Close to 143B.

*Pedicel* (*individual flower stem*).—Length: About 2.6 cm. Diameter: About 1 mm. Strength: Moderately strong. Angle: Mostly upright. Texture: Smooth, glabous. Color: Close to 59A.

*Reproductive organs*.—Androecium: Stamen quantity per flower: About five. Filament length: About 2.6 mm. Filament color: Close to 67A. Anther length: About 1.2 mm. Anther shape: Oblong. Anther color: Close to 185A. Pollen amount: Moderate. Pollen color: Close to 28A. Gynoecium: Pistil quantity per flower: One. Pistil length: About 3.3 mm. Stigma shape: Decurrent. Stigma color: Close to 59C. Style length: About 2 mm. Style color: Close to 59D. Ovary color: Close to 194A.

*Fruits and seeds*.—Fruit and seed development has not been observed on plants of the new *Pelargonium*.

Disease & pest resistance: Plants of the new *Pelargonium* have not been observed to be resistant to pathogens and pests common to *Pelargonium* plants.

Garden performance: Plants of the new *Pelargonium* have been observed to have good garden performance and to tolerate rain, wind and temperatures ranging from about 4° C. to 45° C.

It is claimed:

1. A new and distinct *Pelargonium* plant named 'Duepelsurneviol17' as illustrated and described.

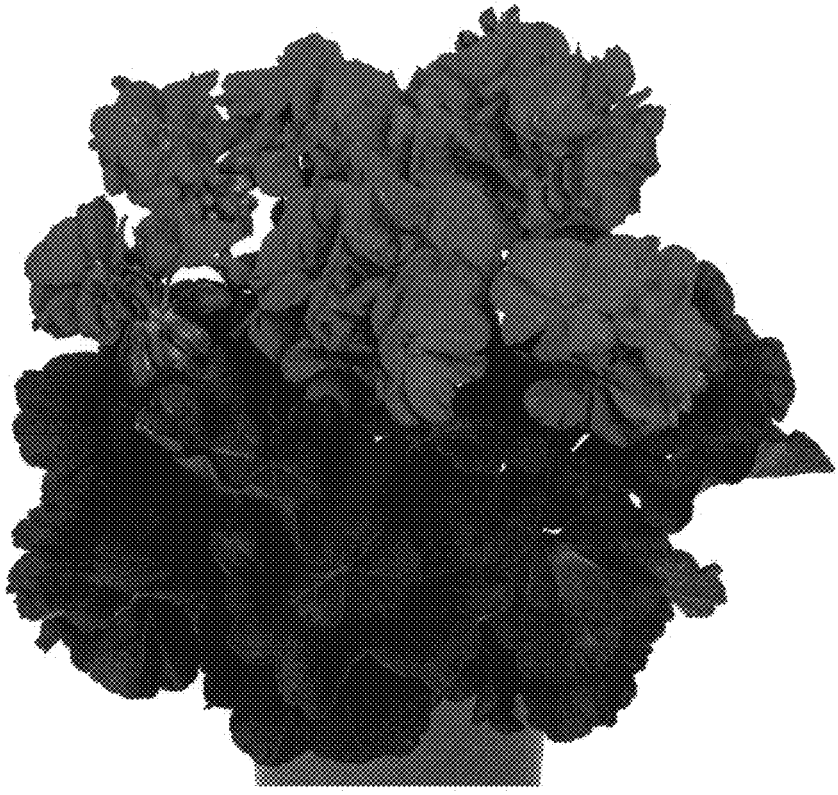

* * * * *